(12) United States Patent
Simmons et al.

(10) Patent No.: US 10,117,978 B2
(45) Date of Patent: Nov. 6, 2018

(54) DRESSING INTERFACE WITH MOISTURE CONTROLLING FEATURE AND SEALING FUNCTION

(71) Applicant: KCI Licensing, Inc., San Antonio, TX (US)

(72) Inventors: Tyler H. Simmons, San Antonio, TX (US); Colin John Hall, Poole (GB); Timothy Mark Robinson, Basingstoke (GB); Richard Marvin Kazala, Jr., San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 671 days.

(21) Appl. No.: 14/339,931

(22) Filed: Jul. 24, 2014

(65) Prior Publication Data

US 2015/0057624 A1    Feb. 26, 2015

Related U.S. Application Data

(60) Provisional application No. 61/870,080, filed on Aug. 26, 2013.

(51) Int. Cl.
*A61F 13/02*  (2006.01)
*A61M 1/00*  (2006.01)
(Continued)

(52) U.S. Cl.
CPC ..... *A61M 1/0088* (2013.01); *A61F 13/00068* (2013.01); *A61F 13/0206* (2013.01);
(Continued)

(58) Field of Classification Search
CPC ............ A61F 13/00068; A61F 13/0206; A61F 13/0223; A61F 2013/0028; A61M 1/0088; A61M 27/00
See application file for complete search history.

(56) References Cited

U.S. PATENT DOCUMENTS 1,355,846 A    10/1920  Rannells
2,547,758 A    4/1951   Keeling
(Continued)

FOREIGN PATENT DOCUMENTS

AU    550575 A1    3/1986
AU    745271       4/1999
(Continued)

OTHER PUBLICATIONS

International Search Report and Written Opinion for PCT/US2014/056508 dated Dec. 9, 2014.
(Continued)

*Primary Examiner* — Tatyana Zalukaeva
*Assistant Examiner* — Kai Weng

(57) ABSTRACT

Provided are systems, dressings, and methods suitable for treating a tissue site, such as an incision or linear wound. The systems, dressings, and methods relate to a dressing assembly that may include a dressing bolster and a sealing ring. The sealing ring may be adapted to provide a fluid seal around the tissue site, and to absorb fluids from the tissue site. In some embodiments, the sealing ring may be extruded around the tissue site. In other embodiments, the sealing ring may be coupled to the dressing bolster. Other systems, apparatuses, and methods are disclosed.

23 Claims, 10 Drawing Sheets

(51) Int. Cl.
*A61F 13/00* (2006.01)
*A61M 27/00* (2006.01)

(52) U.S. Cl.
CPC .. *A61F 13/0223* (2013.01); *A61F 2013/0028* (2013.01); *A61M 27/00* (2013.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,172,808 A | 3/1965 | Baumann et al. |
| 3,367,332 A | 2/1968 | Groves |
| 3,376,868 A | 4/1968 | Mondiadis |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,742,952 A | 7/1973 | Magers et al. |
| 3,774,611 A | 11/1973 | Tussey et al. |
| 3,777,016 A | 12/1973 | Gilbert |
| 3,779,243 A | 12/1973 | Tussey et al. |
| 3,826,254 A | 7/1974 | Mellor |
| 3,852,823 A | 12/1974 | Jones |
| 3,967,624 A | 7/1976 | Milnamow |
| 3,983,297 A | 9/1976 | Ono et al. |
| 4,080,970 A | 3/1978 | Miller |
| 4,096,853 A | 6/1978 | Weigand |
| 4,139,004 A | 2/1979 | Gonzalez, Jr. |
| 4,141,361 A | 2/1979 | Snyder |
| 4,163,822 A | 8/1979 | Walter |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,360,015 A | 11/1982 | Mayer |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,414,970 A | 11/1983 | Berry |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,529,402 A | 7/1985 | Weilbacher et al. |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,664,652 A | 5/1987 | Weilbacher |
| 4,664,662 A | 5/1987 | Webster |
| 4,710,165 A | 12/1987 | McNeil et al. |
| 4,715,857 A | 12/1987 | Juhasz et al. |
| 4,733,659 A | 3/1988 | Edenbaum et al. |
| 4,743,232 A | 5/1988 | Kruger |
| 4,753,230 A | 6/1988 | Carus et al. |
| 4,758,220 A | 7/1988 | Sundblom et al. |
| 4,787,888 A | 11/1988 | Fox |
| 4,826,494 A | 5/1989 | Richmond et al. |
| 4,832,008 A | 5/1989 | Gilman |
| 4,838,883 A | 6/1989 | Matsuura |
| 4,840,187 A | 6/1989 | Brazier |
| 4,848,364 A | 7/1989 | Bosman |
| 4,863,449 A | 9/1989 | Therriault et al. |
| 4,871,611 A | 10/1989 | LeBel |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,930,997 A | 6/1990 | Bennett |
| 4,941,882 A | 7/1990 | Ward et al. |
| 4,953,565 A | 9/1990 | Tachibana et al. |
| 4,961,493 A | 10/1990 | Kaihatsu |
| 4,969,880 A | 11/1990 | Zamierowski |
| 4,981,474 A | 1/1991 | Bopp et al. |
| 4,985,019 A | 1/1991 | Michelson |
| 4,995,382 A | 2/1991 | Lang et al. |
| 4,996,128 A | 2/1991 | Aldecoa et al. |
| 5,010,883 A | 4/1991 | Rawlings et al. |
| 5,018,515 A | 5/1991 | Gilman |
| 5,037,397 A | 8/1991 | Kalt et al. |
| 5,086,170 A | 2/1992 | Luheshi et al. |
| 5,092,323 A | 3/1992 | Riedel et al. |
| 5,092,858 A | 3/1992 | Benson et al. |
| 5,100,396 A | 3/1992 | Zamierowski |
| 5,112,323 A | 5/1992 | Winkler et al. |
| 5,134,994 A | 8/1992 | Say |
| 5,149,331 A | 9/1992 | Ferdman et al. |
| 5,151,314 A | 9/1992 | Brown |
| 5,152,757 A | 10/1992 | Eriksson |
| 5,167,613 A | 12/1992 | Karami et al. |
| 5,176,663 A | 1/1993 | Svedman et al. |
| 5,180,375 A | 1/1993 | Feibus |
| 5,215,522 A | 6/1993 | Page et al. |
| 5,232,453 A | 8/1993 | Plass et al. |
| 5,261,893 A | 11/1993 | Zamierowski |
| 5,266,372 A | 11/1993 | Arakawa et al. |
| 5,270,358 A | 12/1993 | Asmus |
| 5,278,100 A | 1/1994 | Doan et al. |
| 5,279,550 A | 1/1994 | Habib et al. |
| 5,298,015 A | 3/1994 | Komatsuzaki et al. |
| 5,342,329 A | 8/1994 | Croquevielle |
| 5,342,376 A | 8/1994 | Ruff |
| 5,344,415 A | 9/1994 | DeBusk et al. |
| 5,356,386 A | 10/1994 | Goldberg et al. |
| 5,358,494 A | 10/1994 | Svedman |
| 5,384,174 A | 1/1995 | Ward et al. |
| 5,387,207 A | 2/1995 | Dyer et al. |
| 5,419,769 A | 5/1995 | Devlin et al. |
| 5,423,778 A | 6/1995 | Eriksson et al. |
| 5,429,590 A | 7/1995 | Saito et al. |
| 5,437,622 A | 8/1995 | Carion |
| 5,437,651 A | 8/1995 | Todd et al. |
| 5,445,604 A | 8/1995 | Lang |
| 5,447,492 A | 9/1995 | Cartmell et al. |
| 5,522,808 A | 6/1996 | Skalla |
| 5,527,293 A | 6/1996 | Zamierowski |
| 5,549,584 A | 8/1996 | Gross |
| 5,549,585 A | 8/1996 | Maher et al. |
| 5,556,375 A | 9/1996 | Ewall |
| 5,585,178 A | 12/1996 | Calhoun et al. |
| 5,599,292 A | 2/1997 | Yoon |
| 5,607,388 A | 3/1997 | Ewall |
| 5,634,893 A | 6/1997 | Rishton |
| 5,636,643 A | 6/1997 | Argenta et al. |
| 5,641,506 A | 6/1997 | Talke et al. |
| 5,645,081 A | 7/1997 | Argenta et al. |
| 5,653,224 A | 8/1997 | Johnson |
| 5,678,564 A | 10/1997 | Lawrence et al. |
| 5,710,233 A | 1/1998 | Meckel et al. |
| 5,714,225 A | 2/1998 | Hansen et al. |
| 5,736,470 A | 4/1998 | Schneberger et al. |
| 5,776,119 A | 7/1998 | Bilbo et al. |
| 5,807,295 A | 9/1998 | Hutcheon et al. |
| 5,919,476 A | 7/1999 | Fischer et al. |
| 5,941,863 A | 8/1999 | Guidotti et al. |

(56) References Cited

U.S. PATENT DOCUMENTS

| | | | |
|---|---|---|---|
| 6,071,267 A | 6/2000 | Zamierowski |
| 6,086,995 A | 7/2000 | Smith |
| 6,135,116 A | 10/2000 | Vogel et al. |
| 6,174,306 B1 | 1/2001 | Fleischmann |
| 6,191,335 B1 | 2/2001 | Robinson |
| 6,241,747 B1 | 6/2001 | Ruff |
| 6,262,329 B1 | 7/2001 | Brunsveld et al. |
| 6,287,316 B1 | 9/2001 | Agarwal et al. |
| 6,345,623 B1 | 2/2002 | Heaton et al. |
| 6,458,109 B1 | 10/2002 | Henley et al. |
| 6,488,643 B1 | 12/2002 | Tumey et al. |
| 6,493,568 B1 | 12/2002 | Bell et al. |
| 6,495,229 B1 | 12/2002 | Carte et al. |
| 6,548,727 B1 | 4/2003 | Swenson |
| 6,553,998 B2 | 4/2003 | Heaton et al. |
| 6,566,575 B1 | 5/2003 | Stickels et al. |
| 6,566,577 B1 | 5/2003 | Addison et al. |
| 6,626,891 B2 | 9/2003 | Ohmstede |
| 6,648,862 B2 | 11/2003 | Watson |
| 6,680,113 B1 | 1/2004 | Lucast et al. |
| 6,685,681 B2 | 2/2004 | Lockwood et al. |
| 6,693,180 B2 | 2/2004 | Lee et al. |
| 6,695,823 B1 | 2/2004 | Lina et al. |
| 6,752,794 B2 | 6/2004 | Lockwood et al. |
| 6,787,682 B2 | 9/2004 | Gilman |
| 6,814,079 B2 | 11/2004 | Heaton et al. |
| 6,855,135 B2 | 2/2005 | Lockwood et al. |
| 6,856,821 B2 | 2/2005 | Johnson |
| 6,979,324 B2 | 12/2005 | Bybordi et al. |
| 7,070,584 B2 | 7/2006 | Johnson et al. |
| 7,154,017 B2 | 12/2006 | Sigurjonsson et al. |
| 7,569,742 B2 | 8/2009 | Haggstrom et al. |
| 7,645,269 B2 | 1/2010 | Zamierowski |
| 8,298,197 B2 | 10/2012 | Eriksson et al. |
| 8,632,523 B2 | 1/2014 | Eriksson et al. |
| 8,764,732 B2 | 7/2014 | Hartwell |
| 9,192,444 B2 | 11/2015 | Locke et al. |
| 2001/0030304 A1 | 10/2001 | Kohda et al. |
| 2001/0051178 A1 | 12/2001 | Blatchford et al. |
| 2002/0009568 A1 | 1/2002 | Bries et al. |
| 2002/0016346 A1 | 2/2002 | Brandt et al. |
| 2002/0065494 A1 | 5/2002 | Lockwood et al. |
| 2002/0077661 A1 | 6/2002 | Saadat |
| 2002/0115951 A1 | 8/2002 | Norstrem et al. |
| 2002/0119292 A1 | 8/2002 | Venkatasanthanam et al. |
| 2002/0120185 A1 | 8/2002 | Johnson |
| 2002/0130064 A1 | 9/2002 | Adams et al. |
| 2002/0143286 A1 | 10/2002 | Tumey |
| 2002/0150270 A1 | 10/2002 | Werner |
| 2002/0150720 A1 | 10/2002 | Howard et al. |
| 2002/0161346 A1 | 10/2002 | Lockwood et al. |
| 2002/0164346 A1 | 11/2002 | Nicolette |
| 2002/0183702 A1 | 12/2002 | Henley et al. |
| 2002/0198504 A1 | 12/2002 | Risk et al. |
| 2003/0014022 A1 | 1/2003 | Lockwood et al. |
| 2003/0109855 A1 | 6/2003 | Solem et al. |
| 2003/0158577 A1 | 8/2003 | Ginn et al. |
| 2003/0212357 A1 | 11/2003 | Pace |
| 2003/0225347 A1 | 12/2003 | Argenta et al. |
| 2003/0225355 A1 | 12/2003 | Butler |
| 2004/0002676 A1 | 1/2004 | Siegwart et al. |
| 2004/0030304 A1 | 2/2004 | Hunt et al. |
| 2004/0064132 A1 | 4/2004 | Boehringer et al. |
| 2004/0077984 A1 | 4/2004 | Worthley |
| 2004/0127836 A1 | 7/2004 | Sigurjonsson et al. |
| 2004/0127862 A1 | 7/2004 | Bubb et al. |
| 2004/0133143 A1 | 7/2004 | Burton et al. |
| 2004/0186239 A1 | 9/2004 | Qin et al. |
| 2004/0219337 A1 | 11/2004 | Langley et al. |
| 2004/0230179 A1 | 11/2004 | Shehada |
| 2005/0034731 A1 | 2/2005 | Rousseau et al. |
| 2005/0054998 A1 | 3/2005 | Poccia et al. |
| 2005/0065484 A1 | 3/2005 | Watson |
| 2005/0070858 A1 | 3/2005 | Lockwood et al. |
| 2005/0101940 A1 | 5/2005 | Radl et al. |
| 2005/0113732 A1 | 5/2005 | Lawry |
| 2005/0131327 A1 | 6/2005 | Lockwood et al. |
| 2005/0137539 A1 | 6/2005 | Biggie et al. |
| 2005/0143694 A1 | 6/2005 | Schmidt et al. |
| 2005/0159695 A1 | 7/2005 | Cullen et al. |
| 2005/0163978 A1 | 7/2005 | Strobech et al. |
| 2005/0233072 A1 | 10/2005 | Stephan et al. |
| 2005/0256437 A1 | 11/2005 | Silcock et al. |
| 2005/0261642 A1 | 11/2005 | Weston |
| 2005/0261643 A1 | 11/2005 | Bybordi et al. |
| 2005/0277860 A1 | 12/2005 | Jensen |
| 2006/0079852 A1 | 4/2006 | Bubb et al. |
| 2006/0154546 A1 | 7/2006 | Murphy et al. |
| 2006/0241542 A1 | 10/2006 | Gudnason et al. |
| 2006/0271020 A1 | 11/2006 | Huang et al. |
| 2007/0027414 A1 | 2/2007 | Hoffman et al. |
| 2007/0078366 A1 | 4/2007 | Haggstrom et al. |
| 2007/0185426 A1 | 8/2007 | Ambrosio et al. |
| 2007/0225663 A1 | 9/2007 | Watt et al. |
| 2007/0265585 A1 | 11/2007 | Joshi et al. |
| 2007/0265586 A1 | 11/2007 | Joshi et al. |
| 2008/0090085 A1 | 4/2008 | Kawate et al. |
| 2008/0119802 A1 | 5/2008 | Riesinger |
| 2008/0149104 A1 | 6/2008 | Eifler |
| 2008/0195017 A1 | 8/2008 | Robinson et al. |
| 2008/0225663 A1 | 9/2008 | Smith et al. |
| 2008/0243044 A1 | 10/2008 | Hunt et al. |
| 2008/0269657 A1* | 10/2008 | Brenneman ........... A61F 15/004 602/41 |
| 2008/0271804 A1 | 11/2008 | Biggie et al. |
| 2009/0088719 A1 | 4/2009 | Driskell |
| 2009/0124988 A1 | 5/2009 | Coulthard |
| 2009/0227969 A1 | 9/2009 | Jaeb et al. |
| 2009/0264807 A1 | 10/2009 | Haggstrom et al. |
| 2009/0326488 A1 | 12/2009 | Budig et al. |
| 2010/0063467 A1 | 3/2010 | Addison et al. |
| 2010/0125259 A1 | 5/2010 | Olson |
| 2010/0159192 A1 | 6/2010 | Cotton |
| 2010/0185163 A1 | 7/2010 | Heagle |
| 2010/0267302 A1 | 10/2010 | Kantner et al. |
| 2010/0305490 A1 | 12/2010 | Coulthard et al. |
| 2010/0324516 A1 | 12/2010 | Braga et al. |
| 2011/0160686 A1 | 6/2011 | Ueda et al. |
| 2011/0171480 A1 | 7/2011 | Mori et al. |
| 2011/0172617 A1 | 7/2011 | Riesinger |
| 2011/0224631 A1 | 9/2011 | Simmons et al. |
| 2011/0244010 A1 | 10/2011 | Doshi |
| 2011/0257617 A1 | 10/2011 | Franklin |
| 2012/0143157 A1 | 6/2012 | Reisinger |
| 2012/0209226 A1* | 8/2012 | Simmons ........... A61M 1/0088 604/319 |
| 2012/0258271 A1 | 10/2012 | Maughan |
| 2013/0030394 A1 | 1/2013 | Locke et al. |
| 2013/0066285 A1 | 3/2013 | Locke et al. |
| 2013/0096518 A1 | 4/2013 | Hall et al. |
| 2013/0152945 A1 | 6/2013 | Locke et al. |
| 2014/0039424 A1 | 2/2014 | Locke |

FOREIGN PATENT DOCUMENTS

| | | |
|---|---|---|
| AU | 755496 | 2/2002 |
| CA | 2005436 | 6/1990 |
| CN | 87101823 A | 8/1988 |
| DE | 26 40 413 A1 | 3/1978 |
| DE | 43 06 478 A1 | 9/1994 |
| DE | 295 04 378 U1 | 10/1995 |
| DE | 202004018245 U1 | 7/2005 |
| EP | 0097517 A1 | 1/1984 |
| EP | 0100148 A1 | 2/1984 |
| EP | 0117632 A2 | 9/1984 |
| EP | 0161865 A2 | 11/1985 |
| EP | 0251810 A2 | 1/1988 |
| EP | 0275353 A2 | 7/1988 |
| EP | 0358302 A2 | 3/1990 |
| EP | 0538917 A1 | 4/1993 |
| EP | 0630629 A1 | 12/1994 |
| EP | 0659390 A2 | 6/1995 |
| EP | 0633758 B1 | 10/1996 |
| EP | 1002846 A1 | 5/2000 |

(56) References Cited

FOREIGN PATENT DOCUMENTS

| | | |
|---|---|---|
| EP | 1018967 B1 | 8/2004 |
| EP | 2578193 A1 | 4/2013 |
| GB | 692578 | 6/1953 |
| GB | 1386800 A | 3/1975 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| GB | 2377939 A | 1/2003 |
| GB | 2392836 A | 3/2004 |
| GB | 2393655 A | 4/2004 |
| GB | 2425487 A | 11/2006 |
| GB | 2452720 A | 3/2009 |
| JP | 4129536 | 4/1992 |
| JP | 2008080137 A | 4/2008 |
| SG | 71559 | 4/2002 |
| WO | 80/02182 | 10/1980 |
| WO | 87/04626 | 8/1987 |
| WO | 8707164 A1 | 12/1987 |
| WO | 90/010424 | 9/1990 |
| WO | 93/09727 | 5/1993 |
| WO | 94/020041 | 9/1994 |
| WO | 96/05873 | 2/1996 |
| WO | 9622753 A1 | 8/1996 |
| WO | 97/18007 | 5/1997 |
| WO | 99/13793 | 3/1999 |
| WO | 99/65542 A1 | 12/1999 |
| WO | 01/36188 A1 | 5/2001 |
| WO | 01/60296 A1 | 8/2001 |
| WO | 0243743 A1 | 6/2002 |
| WO | 02062403 A1 | 8/2002 |
| WO | 03-018098 A2 | 3/2003 |
| WO | 03045294 A1 | 6/2003 |
| WO | 03045492 A1 | 6/2003 |
| WO | 03053484 A1 | 7/2003 |
| WO | 2004024197 A1 | 3/2004 |
| WO | 2004037334 A1 | 5/2004 |
| WO | 2004112852 A1 | 12/2004 |
| WO | 2005002483 A2 | 1/2005 |
| WO | 2005062896 A2 | 7/2005 |
| WO | 2005105176 A1 | 11/2005 |
| WO | 2007022097 A2 | 2/2007 |
| WO | 2007030601 A2 | 3/2007 |
| WO | 2007070269 A1 | 6/2007 |
| WO | 2007085396 A1 | 8/2007 |
| WO | 2007087811 A1 | 8/2007 |
| WO | 2007113597 A2 | 10/2007 |
| WO | 2007133618 A2 | 11/2007 |
| WO | 2008041926 A1 | 4/2008 |
| WO | 2008054312 A1 | 5/2008 |
| WO | 2008/082444 A2 | 7/2008 |
| WO | 2008/100440 A1 | 8/2008 |
| WO | 2008104609 A1 | 9/2008 |
| WO | 2008/131895 A1 | 11/2008 |
| WO | 2009/002260 A1 | 12/2008 |
| WO | 2009066105 A1 | 5/2009 |
| WO | 2009066106 A1 | 5/2009 |
| WO | 2009081134 A1 | 7/2009 |
| WO | 2009089016 A1 | 7/2009 |
| WO | 2009/124100 A1 | 10/2009 |
| WO | 2010032728 A1 | 3/2010 |
| WO | 2010/056977 A2 | 5/2010 |
| WO | 2010129299 A2 | 11/2010 |
| WO | 2011008497 A2 | 1/2011 |
| WO | 2011043786 A1 | 4/2011 |
| WO | 2011049562 A1 | 4/2011 |
| WO | 2011115908 A1 | 9/2011 |
| WO | 2011121127 A1 | 10/2011 |
| WO | 2012104584 A1 | 8/2012 |
| WO | 2012112204 A1 | 8/2012 |
| WO | 2012140378 A1 | 10/2012 |
| WO | 2012143665 A1 | 10/2012 |
| WO | 2013009239 A1 | 1/2013 |
| WO | 2013090810 A1 | 6/2013 |
| WO | 2014/113253 A1 | 7/2014 |
| WO | 2014140608 A1 | 9/2014 |
| WO | 2014143488 A1 | 9/2014 |
| WO | 2015/065615 A1 | 5/2015 |
| WO | 2015130471 A1 | 9/2015 |

OTHER PUBLICATIONS

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
International Search Report and Written Opinion for PCT/GB2008/003075 dated Mar. 11, 2010.
International Search Report and Written Opinion for PCT/GB2008/004216 dated Jul. 2, 2009.
International Search Report and Written Opinion for PCT/GB2012/000099 dated May 2, 2012.
EP Examination Report for corresponding application 12705381.7, dated May 22, 2014.
International Search Report and Written Opinion for PCT/US2012/069893 dated Apr. 8, 2013.
International Search Report and Written Opinion for PCT/US2013/070070 dated Jan. 29, 2014.
International Search Report and Written Opinion for PCT/US2014/016320 dated Apr. 15, 2014.
International Search Report and Written Opinion for PCT/US2014/056566 dated Dec. 5, 2014.
International Search Report and Written Opinion for PCT/US2014/056524 dated Dec. 11, 2014.
International Search Report and Written Opinion for PCT/US2014/056594 dated Dec. 2, 2014.
Partial Internationl Search Report date dated Jul. 31, 2009; PCT Internationl Application No. PCT/US2009/036222.
International Search Report and Written opinion dated Dec. 15, 2009; PCT Internation Application No. PCT/US2009/036222.
International Search Report and Written Opinion dated Feb. 24, 2010; PCT/US2009/057182.
International Search Report and Written Opinion dated Jan. 5, 2010; PCT International Application No. PCT/US2009/057130.
Response filed Oct. 20, 2011 for U.S. Appl. No. 12/398,904.
Interview Summary dated Oct. 27, 2011 for U.S. Appl. No. 12/398,904.
Non-Final Office Action dated Jul. 20, 2011 for U.S. Appl. No. 12/398,904.
NDP 1000 Negative Pressure Wound Terapy System, Kalypto Medical, pp. 1-4.
Partial International Search Report dated Jul. 31, 2009 for PCT International Application No. PCT/US2009/036217.
International Search Report and Written Opinion dated May 31, 2010 for PCT Application No. PCT/US2009/064364.
Examination report for AU2009221772 dated Apr. 4, 2011.
Response filed Oct. 21, 2011 for U.S. Appl. No. 12/398,891.
Interview Summary dated Oct. 27, 2011 for U.S. Appl. No. 12/398,891.
Restriction Requirement dated Jun. 13, 2011 for U.S. Appl. No. 12/398,891.
Response filed Jun. 24, 2011 for U.S. Appl. No. 12/398,891.
Non-Final Office Action dated Jul. 21, 2011 for U.S. Appl. No. 12/398,891.
International Search Report and Written Opinion dated Oct. 19, 2010; PCT International Application No. PCT/US2009/036217.
International Search Report and Written Opinion dated Feb. 24, 2010; PCT International Application No. PCT/US2009/057182.
NPD 1000 Negative Pressure Would Therapy System, Kalypto Medical, pp. 1-4.
Partial International Search Report dated Jul. 31, 2009; PCT Internationl Application No. PCT/US2009/036222.
Non-Final Rejection for U.S. Appl. No. 12/398,904 dated Mar. 14, 2012.
Response to Non-Final Rejection for U.S. Appl. No. 12/398,904, filed Jun. 4, 2012.

(56) References Cited

OTHER PUBLICATIONS

International Search Report and Written Opinion for PCT/US2014/061251 dated May 8, 2015.
International Search Report and Written Opinion for PCT/IB2013/060862 dated Jun. 26, 2014.
International Search Report and Written Opinion for PCT/US2015/015493 dated May 4, 2015.
European Search Report for corresponding Application No. 15194949.2.
European Search Report for corresponding EPSN 15157408.4 published on Sep. 30, 2015.
International Search Report and Written Opinion for PCT/US2015/029037 dated Sep. 4, 2015.
International Search Report and Written Opinion for PCT/US2015/034289 dated Aug. 21, 2015.
International Search Report and Written Opinion for PCT/US2015/065135 dated Apr. 4, 2016.
International Search Report and Written Opinion for PCT/GB2012/050822 dated Aug. 8, 2012.
International Search Report and Written Opinion dated Jun. 1, 2011 for PCT International Application No. PCT/US2011/028344.
European Search Report for EP 11714148.1, dated May 2, 2014.
European Search Report for corresponding Application No. 15192606.0 dated Feb. 24, 2016.
European Examination Report dated Jun. 29, 2016, corresponding to EP Application No. 16173614.5.
International Search Report and Written Opinion for corresponding PCT/US2014/010704 dated Mar. 25, 2014.
International Search Report and Written Opinion for corresponding PCT/US2014/048081 dated Nov. 14, 2014.
N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (copy and certified translation).
Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Ðukic, Ž. Maksimović, Ð. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union

(56) References Cited

OTHER PUBLICATIONS

Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians (Jul. 2007).

International Search Report and Written Opinion for corresponding PCT application PCT/US2016/051768 dated Dec. 15, 2016.

* cited by examiner

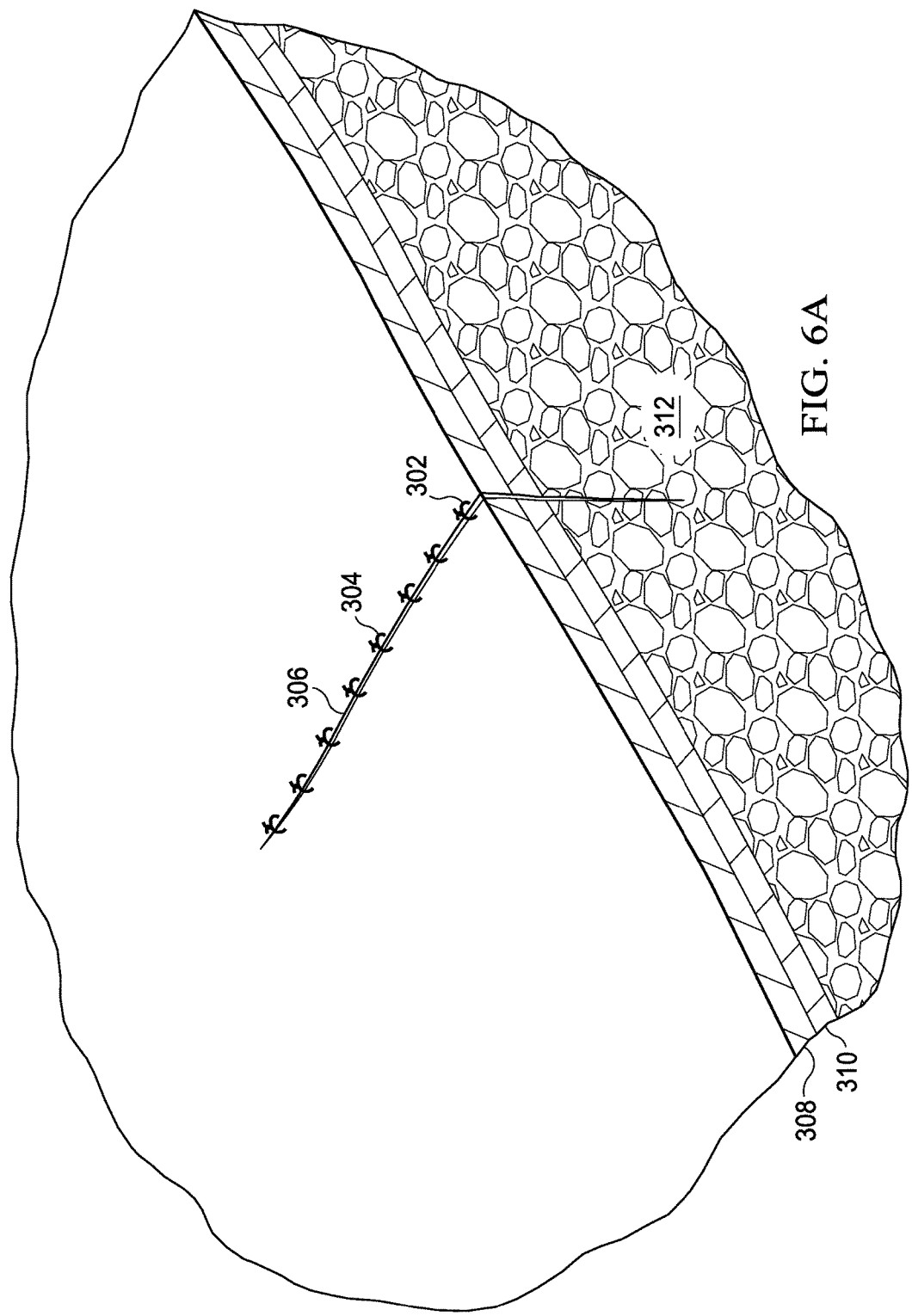

DRESSING INTERFACE WITH MOISTURE CONTROLLING FEATURE AND SEALING FUNCTION

RELATED APPLICATION

This application claims the benefit, under 35 USC § 119(e), of the filing of U.S. Provisional Patent Application Ser. No. 61/870,080, entitled "DRESSING INTERFACE WITH MOISTURE CONTROLLING FEATURE AND SEALING FUNCTION," filed Aug. 26, 2013, which is incorporated herein by reference for all purposes.

BACKGROUND

This application relates generally to medical treatment systems and, more particularly, but not by way of limitation, to reduced pressure dressings, systems, and methods for treating linear wounds.

Clinical studies and practice have shown that providing a reduced pressure in proximity to a tissue site may augment and accelerate the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") may provide a number of benefits, which may include faster healing and increased formulation of granulation tissue. Typically, reduced pressure is applied to tissue through a porous pad or other manifold device. The porous pad may distribute reduced pressure to the tissue and channel fluids that are drawn from the tissue.

SUMMARY

According to an illustrative embodiment, provided is a system for treating a tissue site that may include a dressing assembly and a reduced-pressure source. The dressing assembly may include a dressing bolster, a comfort layer, a first sealing member, a second sealing member, and a sealing ring. The dressing bolster may have a first side and a second side. The comfort layer may be coupled to the second side of the dressing bolster. The first sealing member may cover the first side of the dressing bolster. The second sealing member may cover a portion of the second side of the dressing bolster and extend outward from the dressing bolster to form a drape extension. A portion of the first sealing member may be coupled to the second sealing member. The sealing ring may be disposed adjacent to the second side of the dressing bolster and may be comprised of a hydrocolloid including an absorbent. The first sealing member, the second sealing member, and the sealing ring may be configured to provide a sealed space over the tissue site. The reduced-pressure source may be configured to be coupled in fluid communication with the sealed space.

According to another illustrative embodiment, provided is a system for treating a tissue site that may include a dressing assembly, a sealing member, and a reduced-pressure source. The dressing assembly may include a dressing bolster, a comfort layer, and a sealing ring. The dressing bolster may have a first side and a second side. The comfort layer may have a first side and a second side, and the first side of the comfort layer may be coupled to the second side of the dressing bolster. The sealing ring may be coupled to the second side of the comfort layer, and the sealing ring may include an absorbent. The sealing member may be configured to cover the dressing assembly and to create a sealed space between the dressing assembly and the tissue site. The reduced-pressure source may be configured to be coupled in fluid communication with the sealed space.

According to another illustrative embodiment, provided is a dressing assembly that may include a dressing bolster, a comfort layer, and a sealing ring. The dressing bolster may comprise a foam and may have a first side and a second side. The comfort layer may have a first side and a second side, and the first side of the comfort layer may be coupled to the second side of the dressing bolster. The sealing ring may comprise an absorbent and may have a first side and a second side. The first side of the sealing ring may be coupled to the second side of the comfort layer and may be positioned around a circumference of the dressing bolster. At least a portion of the second side of the comfort layer may be exposed.

According to another illustrative embodiment, provided is a method for treating a tissue site that may include disposing a dressing assembly proximate to the tissue site. The dressing assembly may include a dressing bolster, a comfort layer, and a sealing ring. The comfort layer may be coupled to the dressing bolster, and the sealing ring may be coupled to the comfort layer. The method may additionally include covering the dressing assembly with a sealing member to form a sealed space between the dressing assembly and the tissue site. Further, the method may include extracting fluid from the tissue site and into the dressing assembly, and absorbing the fluid from the tissue site into the sealing ring.

Other features and advantages of the illustrative embodiments will become apparent with reference to the drawings and detailed description that follow.

BRIEF DESCRIPTION OF THE DRAWINGS

FIGS. 6A-6C are perspective views, with a portion shown in cross-section, of a portion of an illustrative embodiment of a treatment system being deployed over a linear wound.

DETAILED DESCRIPTION OF ILLUSTRATIVE EMBODIMENTS

In the following detailed description of the illustrative embodiments, reference is made to the accompanying drawings that form a part hereof. These embodiments are described in sufficient detail to enable those skilled in the art to practice the subject matter of this disclosure. Other embodiments may be utilized, and logical, structural, mechanical, electrical, and chemical changes may be made without departing from the scope of this disclosure. To avoid detail not necessary to enable those skilled in the art to practice the embodiments described herein, the description may omit certain information known to those skilled in the art. Therefore, the following detailed description is non-limiting, with the scope of the illustrative embodiments being defined by the appended claims.

Figure 1:
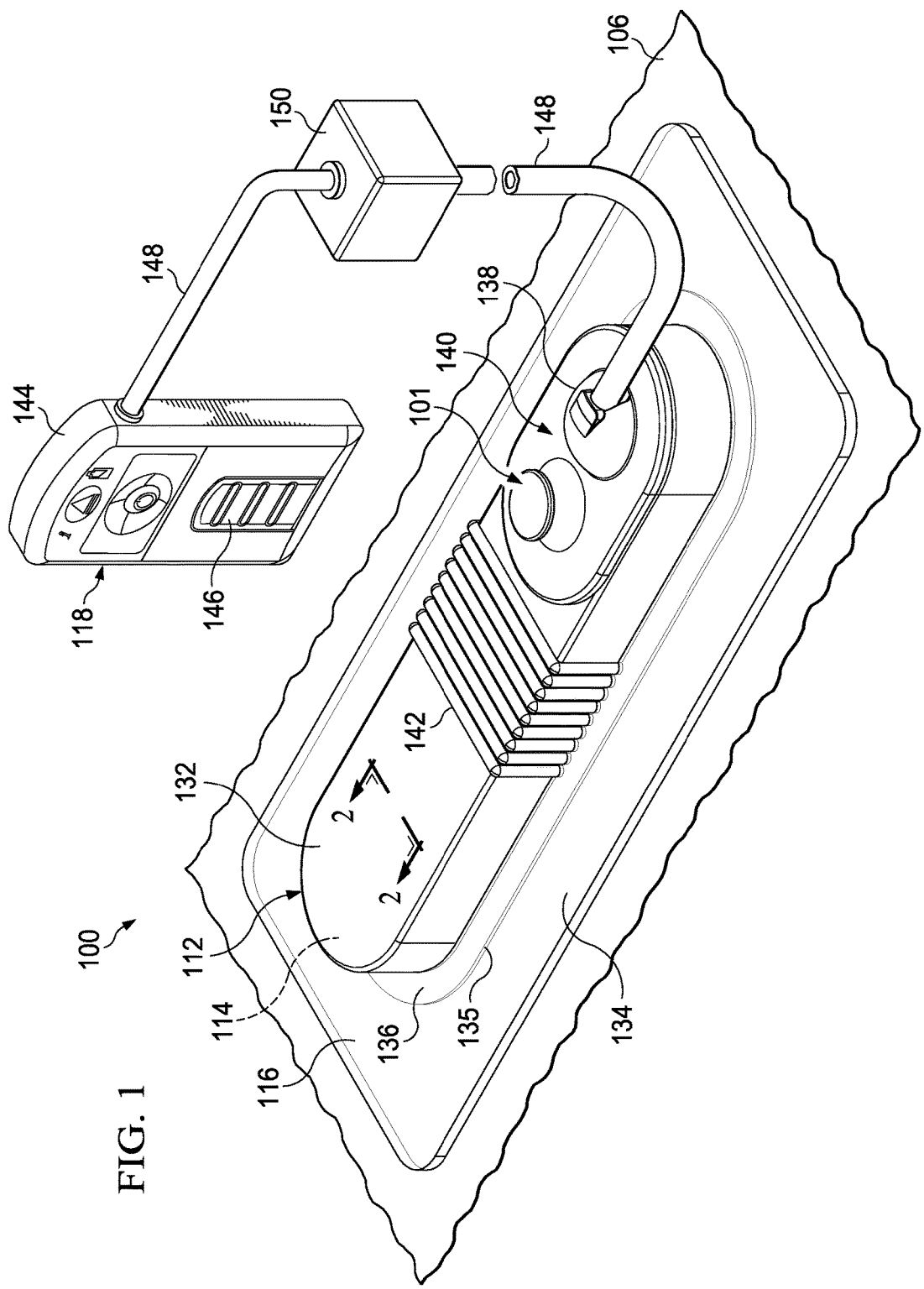
FIG. 1 is a perspective view of an illustrative embodiment of a system for treating a tissue site.
Figure 2:
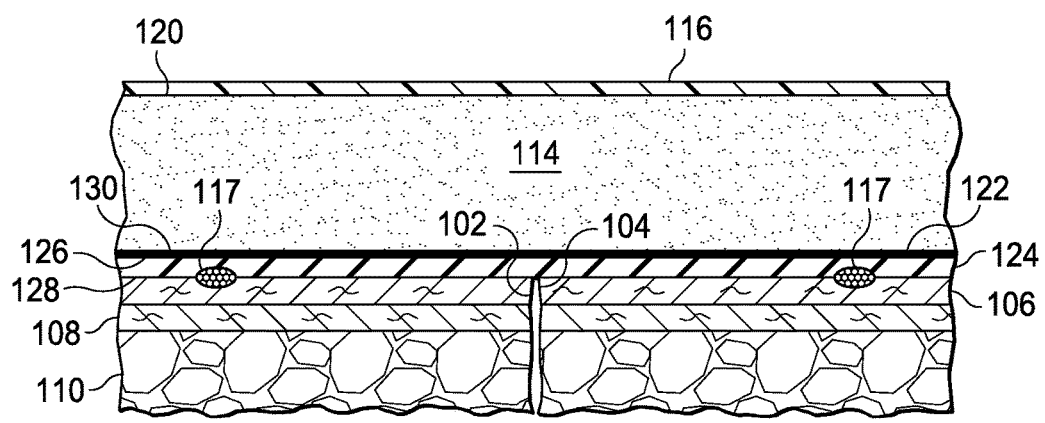
FIG. 2 is a cross-section of a portion of an illustrative embodiment of a dressing assembly depicted in FIG. 1, taken along line 2-2.

Referring primarily to FIGS. 1 and 2, an illustrative, non-limiting embodiment of a treatment system 100 for treating a tissue site 102, such as a an incision 104, is presented. The incision 104 is shown extending through or involving epidermis 106, dermis 108, and subcutaneous tissue 110. The treatment system 100 may also be used with other tissue sites, and may be utilized with or without reduced pressure as described herein.

The treatment system 100 may include a dressing assembly 112 having a dressing bolster 114, or manifold member 114. In addition, the treatment system 100 may include a sealing member 116 and a reduced-pressure subsystem 118. The treatment system 100 may also include a reduced-pressure indicator 101. While the treatment system 100 is shown in the context of a reduced-pressure dressing over an incision 104, the treatment system 100 may be used on other tissue sites, including open wounds.

The dressing bolster 114 has a first side 120 and a second, inward-facing side 122. The dressing bolster 114 may be formed from any bolster material or manifold material that provides a vacuum space, or treatment space. For example, the dressing bolster 114 may be formed from a porous and permeable foam or foam-like material, a member formed with pathways, a graft, a gauze, or any combination thereof. In some embodiments, the dressing bolster 114 may be a reticulated, open-cell polyurethane or polyether foam that may be fluid permeable. Reduced pressure applied to the dressing bolster 114 may enhance the permeability of the dressing bolster 114. One such foam material may be a VAC® GranuFoam® material available from Kinetic Concepts, Inc. (KCI) of San Antonio, Tex. The term "manifold" as used herein may refer to a substance or structure that may assist in applying reduced pressure to, delivering fluids to, or removing fluids from a tissue site. A manifold may include a plurality of flow channels or pathways. The plurality of flow channels may be interconnected to improve distribution of fluids provided to and removed from the area of tissue around the manifold. Examples of manifolds may include, without limitation, devices that have structural elements arranged to form flow channels, cellular foam, such as open-cell foam, porous tissue collections, and liquids, gels, and foams that include or cure to include flow channels.

The reticulated pores of the GranuFoam® material may be helpful in carrying out the manifold function, but as stated above, other materials may be utilized. A material with a higher or lower density than the GranuFoam® material may be desirable in some embodiments. This material may have, for example, a smaller pore size than the GranuFoam® material. Among the many possible materials, the following may be used: GranuFoam® material, FXI technical foam (www.fxi.com), gauze, a flexible channel-containing member, a graft, and other similar materials. In some embodiments, ionic silver may be added to the material, such as, for example, by a micro bonding process. Other substances, such as antimicrobial agents, may also be added to the material.

A comfort layer 124 having a first side 126 and a second, inward-facing side 128 may be coupled, for example, by a heat bond 130 or other suitable technique to the second, inward-facing side 122 of the dressing bolster 114. The comfort layer 124 may enhance patient comfort when the dressing bolster 114 is adjacent to the epidermis 106 of a patient. The comfort layer 124 may be any material that helps prevent skin irritation and discomfort while allowing fluid transmission through the comfort layer 124. As non-limiting examples, a woven material, an elastic material, a polyester knit textile substrate, a non-woven material, or a fenestrated film may be utilized. As another non-limiting example, an InterDry™ textile material from Milliken Chemical, a division of Milliken & Company, Inc. of Spartanburg, S.C., may be utilized. In some embodiments, the comfort layer 124 may include antimicrobial substances, such as silver.

Figure 4:
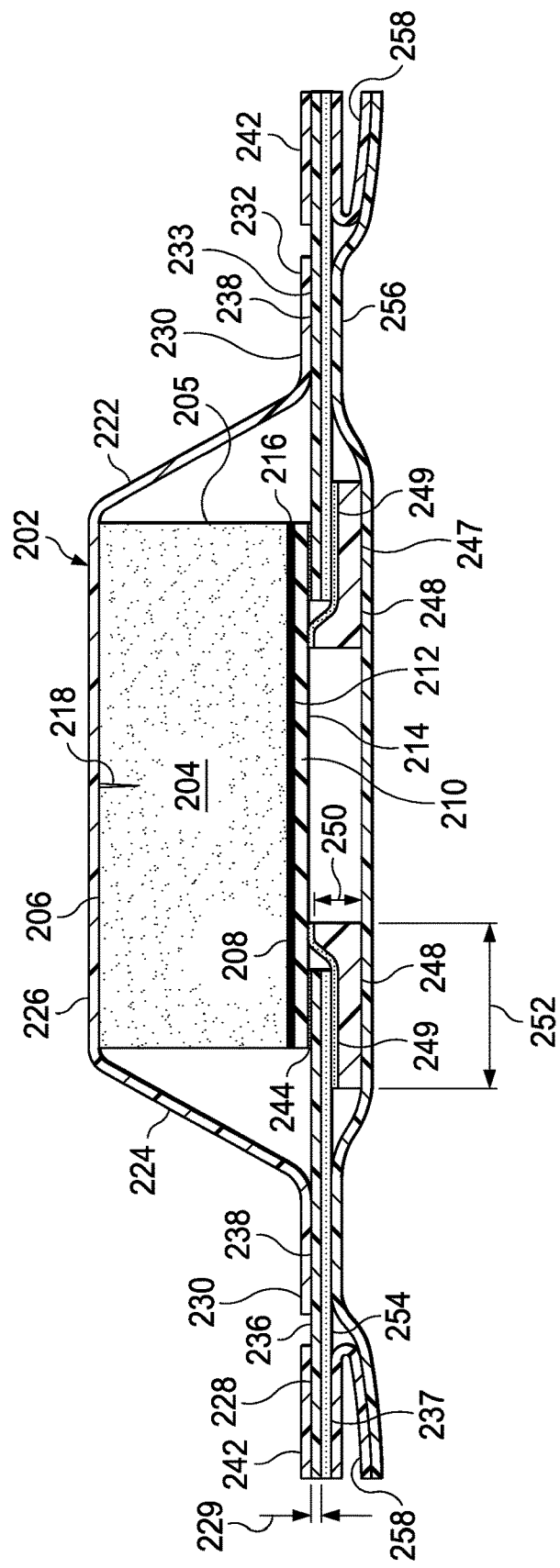
FIG. 4 is a cross-section of an illustrative embodiment of a dressing assembly depicted in FIG. 3, taken along line 4-4.

The dressing bolster 114 may include a plurality of flexibility notches or recesses, analogous to notches 218 shown in FIG. 4, for example, that may be lateral cuts in the dressing bolster 114 on the first side 120. The dressing bolster 114 may include one or more longitudinal cuts or notches. The flexibility notches may enhance the flexibility of the dressing bolster 114. The enhanced flexibility may be particularly useful when the dressing assembly 112 is applied over a joint or other area of movement on a patient. The flexibility notches may also take various shapes without limitation, such as, for example, hexagons, slits, or squares.

The dressing bolster 114 may have lateral edges (not shown) that are orthogonal with respect to the second, inward-facing side 122 of the dressing bolster 114. The lateral edges of the dressing bolster 114 may be analogous to lateral edges 205 of dressing bolster 204 depicted in FIG. 4. The lateral edges of the dressing bolster 114 may also have a beveled edge or angled edge. The angled or beveled edge may help distribute shear stress between the dressing bolster 114 and the epidermis 106 of a patient. The lateral edges of the dressing bolster 114 may substantially correspond to lateral edges (not shown) of the comfort layer 124.

The sealing member 116 may provide a fluid seal over the dressing bolster 114 and at least a portion of the epidermis 106 of the patient. As such, the sealing member 116 may be formed from any material that allows for a fluid seal. "Fluid seal," or "seal," may be a seal adequate to maintain reduced pressure at a desired site given the particular reduced-pressure source or subsystem involved. The sealing member 116 may be sealed against the epidermis 106, or against a gasket or drape, by a sealing apparatus, such as, for example, a pressure-sensitive adhesive.

The sealing apparatus may take numerous forms, such as an adhesive sealing tape, drape tape, or strip; double-side drape tape; pressure-sensitive adhesive; paste; hydrocolloid; hydrogel; or other suitable sealing device. If a tape is used, the tape may be formed of the same material as the sealing member 116 with a pre-applied, pressure-sensitive adhesive. The pressure-sensitive adhesive may be applied on a side of the sealing member 116 adapted to face the epidermis 106, such as an inward-facing side of the sealing member 116. The pressure-sensitive adhesive may provide a fluid seal between the sealing member 116 and the epidermis, and may be utilized in combination with a gasket or drape against the epidermis 106. Before the sealing member 116 is secured to the epidermis 106, removable strips or release liners that cover the pressure-sensitive adhesive may be removed.

The sealing member 116 may be an elastomeric material or any material or substance that provides a fluid seal. "Elastomeric" may refer to a material having the properties of an elastomer, such as a polymeric material that has rubber-like properties. Some elastomers may have ultimate elongations greater than 100% and a significant amount of resilience. The resilience of a material may refer to the ability of the material to recover from an elastic deformation. Examples of elastomers may include, without limitation, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. Further, sealing member materials may include a silicone drape, a 3M Tegaderm® drape, an acrylic drape, such as one available from Avery Dennison, or an incise drape.

The sealing member 116 may be comprised of a material having a high moisture vapor transmission rate (MVTR). Use of a high MVTR material for the sealing member 116 may permit moisture vapor to pass through the sealing member 116, external to the dressing assembly 112, while maintaining the fluid seal described above.

The sealing member 116 may include a first sealing member portion 132 and a second sealing member portion 134. The first sealing member portion 132 may extend over the first side 120 of the dressing bolster 114. The sealing member 116 may extend further to form a sealing member flange, or sealing member extension 136, which has a first side (not shown) and a second, inward-facing side (not shown). The second, inward-facing side of the sealing member extension 136 may be adapted to face the epidermis 106. An aperture (not shown) may be formed on a portion of the sealing member 116 to allow fluid communication with a conduit interface 138, which may be part of a reduced-pressure assembly 140. The aperture on the sealing member 116 may be analogous to aperture 234 depicted in FIG. 3.

The second, inward-facing side of the sealing member extension 136 may be placed on a first side (not shown) of the second sealing member portion 134, and coupled, such as by an adhesive, a bond 135, a weld (e.g., ultrasonic or RF welding), or by cements. The first side of the second sealing member portion 134 may face away from the epidermis 106. In another embodiment, the first sealing member portion 132 and the second sealing member portion 134 may be integrally formed with one another. The first sealing member portion 132 may include a plurality of bellows 142, folds, or stretch zones. The bellows 142 may provide additional drape material when needed to respond to stretching or other movement. For example, if the dressing assembly 112 is used on a joint, when the joint is flexed, the bellows 142 may provide additional drape material to facilitate such movement.

Prior to application, one or more release members (not shown) may be releasably coupled to the first side of the second sealing member portion 134. The release members may be analogous to release members 242 depicted in FIG. 5, and may provide stiffness to assist with, for example, deployment of the dressing assembly 112. The release members may be, for example, casting paper or a film held on the first side of the second sealing member portion 134. Each release member may have a release agent disposed on a side of the release member configured to contact a component of the dressing assembly 112, such as the second sealing member portion 134, or other components described below. In some embodiments, the release agent may be a silicone coating and may have a release factor between about 5 grams per centimeter to about 15 grams per centimeter. In other embodiments, the release factor may be between about 2 grams per centimeter to about 6 grams per centimeter. The release agent may facilitate removal of the release member by hand and without damaging or deforming the dressing assembly 112.

Release members suitable for use with the embodiments described herein may be, for example, polyester release members specified as FRA 301(T-36) and FRA 396-T13, available from Fox River Associates, LLC of Geneva, Ill. The polyester release members may be a polyethylene terephthalate (PET) release member as described below. In some embodiments, the release members may have a film thickness between about 30 microns to about 70 microns. In other embodiments, the film thickness between about 47 microns to about 53 microns. Further, the release members may have a tensile break strength in a machine direction between about 9 kilograms per square millimeter to about 15 kilograms per square millimeter. In a transverse direction, or direction transverse to the machine direction, the release members may have a tensile break strength between about 15 kilograms per square millimeter to about 23 kilograms per square millimeter. The elongation at break of the release members in both the machine direction and the transverse direction may be between about 40 percent to about 140 percent. The release members may have a shrinkage in the machine direction between about 0.0 percent to about 2.5 percent, and a shrinkage in the transverse direction between about 0.0 percent to about 1.2 percent.

The reduced-pressure subsystem 118 may include a reduced-pressure source 144. The reduced-pressure source 144 may provide reduced pressure as a part of the treatment system 100. The reduced-pressure source 144 may be fluidly coupled to the conduit interface 138 by a delivery conduit 148.

As used herein, "reduced pressure" may refer to a pressure less than the ambient pressure at a tissue site being subjected to treatment, such as the tissue site 102. The reduced pressure may be less than the atmospheric pressure. The reduced pressure may also be less than a hydrostatic pressure at a tissue site. Unless otherwise indicated, quantitative values of pressure stated herein are gauge pressures.

The reduced pressure delivered to the dressing bolster 114 may be constant or varied, patterned or random, and may be delivered continuously or intermittently. Although the terms "vacuum" and "negative pressure" may be used to describe the pressure applied to a tissue site, the actual pressure applied to the tissue site may be more than the pressure normally associated with a complete vacuum. Consistent with the use herein, unless otherwise indicated, an increase in reduced pressure or vacuum pressure may refer to a relative reduction in absolute pressure.

The reduced-pressure source 144 is shown in FIG. 1 as having a reservoir region 146, or canister region. An interposed membrane filter (not shown), such as hydrophobic or oleophobic filter, may be interspersed between the reduced-pressure delivery conduit 148 and the reduced-pressure source 144. One or more devices, such as a representative device 150, may be fluidly coupled to the reduced-pressure delivery conduit 148. The representative device 150 may be, for example, another fluid reservoir, a collection member to hold exudates and other fluids removed, a pressure-feedback device, a volume detection system, a blood detection system, an infection detection system, a flow monitoring system, or a temperature monitoring system. Multiple representative devices 150 may be included. One or more of the representative devices 150 may be formed integrally with the reduced-pressure source 144.

The reduced-pressure source 144 may be any device for supplying a reduced pressure, such as a vacuum pump, wall suction, or other source. While the amount and nature of reduced pressure applied to a tissue site may vary according to the application, the reduced pressure may be, for example, between about −5 mm Hg (−667 Pa) to about −500 mm Hg (−66.7 kPa). In some embodiments, the reduced pressure may be between about −75 mm Hg (−9.9 kPa) to about −300 mm Hg (−39.9 kPa).

The reduced pressure developed by the reduced-pressure source 144 may be delivered through the delivery conduit 148 to the conduit interface 138. The conduit interface 138 may allow the reduced pressure to be delivered through the sealing member 116 to the dressing bolster 114. In some embodiments, the conduit interface 138 may provide fluid communication external to the sealing member 116 without the application of reduced pressure.

In providing treatment with the treatment system 100, it may be desirable to know that reduced pressure of at least a certain threshold level is being delivered to the tissue site 102. The reduced-pressure indicator 101 may indicate such a threshold pressure. The reduced-pressure indicator 101 may be a separate unit fluidly coupled to the sealing member 116 such that reduced pressure from within the sealed space of the sealing member 116 reaches the reduced-pressure indicator 101. In some embodiments, as shown in FIG. 1, the reduced-pressure indicator 101 may be associated with the conduit interface 138 as a part of the reduced-pressure assembly 140. When adequate reduced pressure is present, the reduced-pressure indicator 101 may assume a collapsed position. When inadequate reduced pressure is present, the reduced-pressure indicator 101 may assume a non-collapsed position.

Referring primarily to FIG. 2, a sealing ring 117 may be added to the dressing assembly 112. The sealing ring 117 may enhance or otherwise provide a fluid seal around the tissue site 102, such as the incision 104. The epidermis 106 may have recesses, cracks, wrinkles, or other discontinuities on a surface of the epidermis 106 that may cause leaks. Moreover, folds, buckles, wrinkles, or other discontinuities may form in the sealing member 116 and cause leaks. These discontinuities may be a considerable issue for low flow treatment systems. The sealing ring 117 may help seal any such skin or sealing member discontinuities around the tissue site 102.

The sealing ring 117 may be adapted to be positioned between the dressing assembly 112 and the epidermis 106 and/or the tissue site 102. The sealing ring 117 may be formed, as an illustrative example, by applying or bonding a ring of sealing material to the dressing assembly 112. The sealing material may include hydrocolloids, hydrogels, silicone polymers (both crosslinked and uncrosslinked gels), and natural gums (xanthan, guar, cellulose). The sealing material may include other soft polymer gels, such as, for example, those based on polyurethanes, polyolefin gels, and acrylics.

The sealing ring 117 may be deployed by hand or extruded from an applicator, such as a syringe, to form a ring prior to application of the dressing assembly 112 to the tissue site 102. Sealing materials suitable for application by extrusion may include water soluble gums such as xanthan, guar, or cellulose, and thick greases, such as silicones. In another embodiment, the sealing ring 117 may be bonded in any suitable manner, such as, for example, by a heat bond, to the second, inward facing side 128 of the comfort layer 124 during manufacture of the dressing assembly 112. In this manner, the sealing ring 117 may be adapted to be positioned between the comfort layer 124 and the epidermis 106 and/or the tissue site 102.

In one embodiment, the sealing ring 117 may include an absorbent. For example, the sealing ring 117 may be a hydrocolloid comprising an absorbent, such as carboxy methyl cellulose (CMC). The absorbent may permit the sealing ring 117 to absorb fluid from the tissue site 102 in addition to enhancing the fluid seal around the tissue site 102. The sealing ring 117 including the absorbent may enhance the ability of the dressing assembly 112 to manage and direct fluid away from the tissue site 102 for keeping the tissue site 102 dry. For example, the dressing bolster 114 may have a thickness between the first side 120 and the second, inward-facing side 122 of the dressing bolster 114. The thickness of the dressing bolster 114 may define at least a portion of a thickness of the dressing assembly 112. The sealing ring 117 may be adapted to be positioned between the dressing assembly 112 and the tissue site 102, as described above, and around or surrounding a circumference of the tissue site 102. Relative to the dressing assembly 112, the sealing ring 117 may be positioned, for example, around, on, or at the lateral edges of the dressing bolster 114 and/or the comfort layer 124. Further, the sealing ring 117 may be positioned around or surrounding a circumference of the dressing bolster 114 and/or the comfort layer 124. Further, the sealing ring 117 may be positioned around at least a portion of the dressing bolster 114 or the comfort layer 124 that is configured to be positioned directly against or in direct contact with the tissue site 102. At least a portion of the dressing bolster 114 and/or the comfort layer 124 may be exposed and configured to be positioned directly against the tissue site 102 when the sealing ring 117 is positioned on the dressing assembly 112. Further, in such embodiments, the sealing ring 117 may surround the exposed portion of the dressing bolster 114 and/or the comfort layer 124.

The absorbent in the sealing ring 117 may wick or draw fluid in a lateral direction within the dressing assembly 112, normal to the thickness of the dressing bolster 114, and toward the lateral edges of the dressing bolster 114 for absorption in the sealing ring 117. Thus, fluid from the tissue site 102 may be wicked or otherwise drawn in a lateral direction along the surface of the tissue site 102 toward the lateral edges of the dressing bolster 114 and into the sealing ring 117. Further, fluid from the tissue site 102 may also flow through the thickness of the dressing assembly 112 and the dressing bolster 114 at least by operation of the manifold material comprising the dressing bolster 114, described above.

Figure 3:
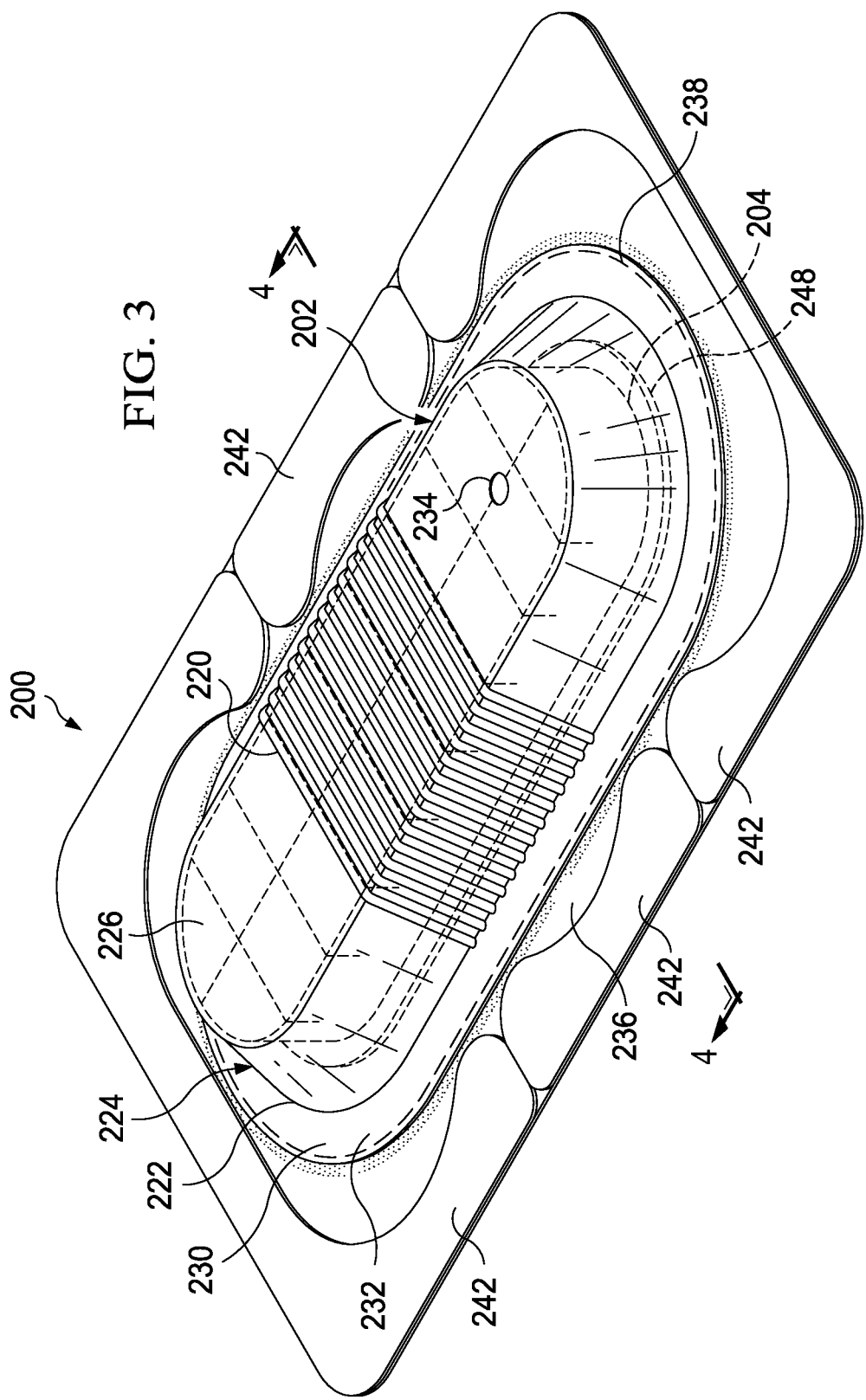
FIG. 3 is a perspective view of an illustrative embodiment of a portion of a treatment system for treating a tissue site.
Figure 5:
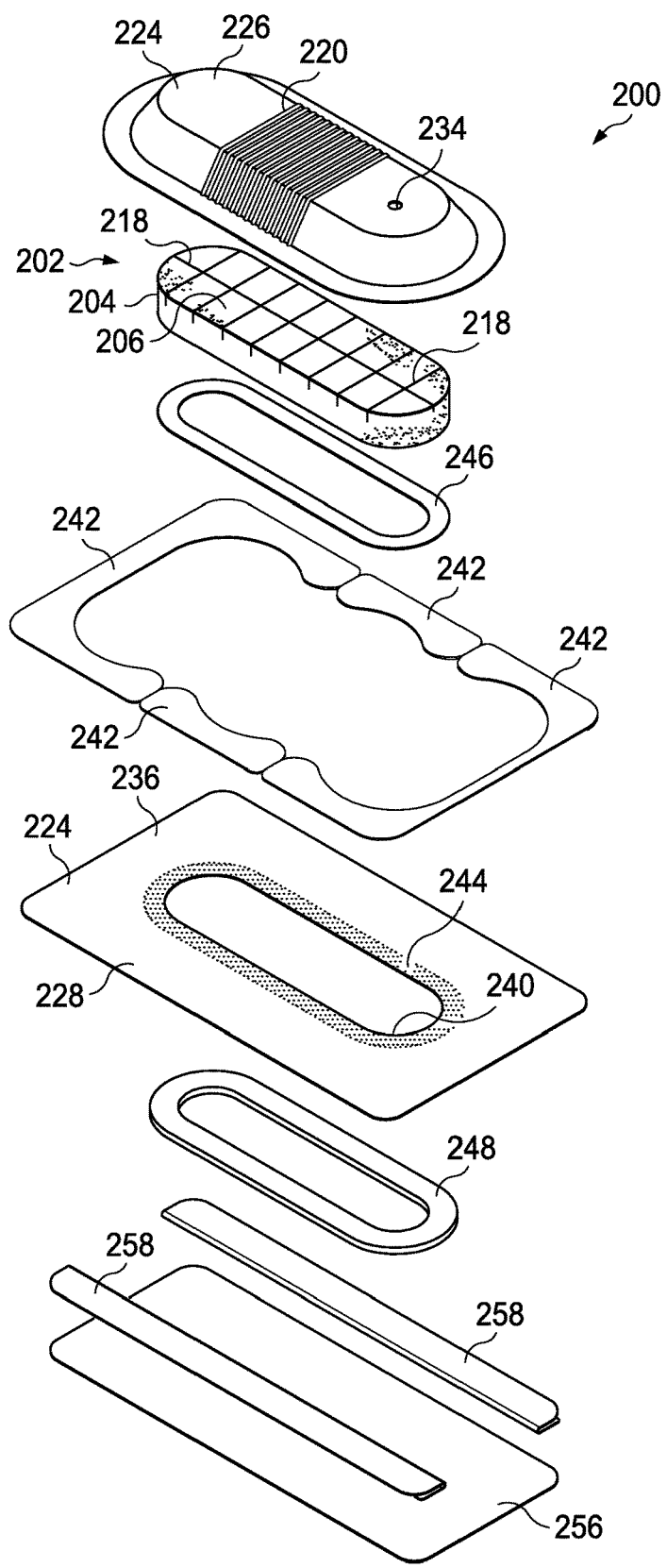
FIG. 5 is an exploded, perspective view of the dressing assembly of FIG. 4 in a state prior to assembly or deployment.

Referring now primarily to FIGS. 3-5, depicted is a portion of a treatment system 200 suitable for treating, for example, a linear wound, area wound, other wound, or a graft. FIGS. 3-5 depict the treatment system 200 in a pre-deployment state. The treatment system 200 includes a dressing assembly 202, and the dressing assembly 202 includes a dressing bolster 204. The dressing bolster 204 has a first side 206 and a second, inward-facing side 208. The dressing bolster 204 may be formed from any suitable bolster material, or manifold material, as previously referenced in connection with the dressing bolster 114. A comfort layer 210, which has a first side 212 and a second, inward-facing side 214, may be coupled, such as, for example, by a heat bond 216 or other suitable technique to the second, inward-facing side 208 of the dressing bolster 204.

The comfort layer 210 may be any material that helps prevent skin irritation and discomfort while allowing fluid transmission through the comfort layer 210. Suitable materials for the comfort layer 210 have been mentioned in connection with the comfort layer 124 of FIGS. 1-2. In some embodiments, the comfort layer 210 may include antimicrobial substances, such as silver. Further, in some embodiments, the comfort layer 210 may be made as a breathable, dry layer.

In some illustrative embodiments, the dressing bolster 204 may include a plurality of flexibility notches 218. The flexibility notches 218 may extend partially through or completely through the dressing bolster 204. The flexibility notches 218 may be lateral notches, or lateral cuts, in the dressing bolster 204. The flexibility notches 218 may also be one or more longitudinal notches, longitudinal cuts, or other cuts. The cuts may be made using a saw, a notched blade, a hot knife, or other device. The flexibility notches 218 may enhance the flexibility of the dressing bolster 204. The enhanced flexibility may be particularly useful when the dressing assembly 202 is applied over a joint or other area of movement on a patient. For example, if the dressing bolster 204 is used on a knee, the dressing bolster 204 may need to flex or extend as much as 100% or more. The flexibility notches 218 may provide such flexibility.

The dressing bolster 204 may have lateral edges 205 that are orthogonal with respect to the second, inward-facing side 208 of the dressing bolster 204. The lateral edges 205 may also have a shape, such as, for example, a beveled, angled, or rounded shape. The lateral edges 205, when angled, may be between about 10 degrees to about 90 degrees with respect to the second, inward-facing side 208 of the dressing bolster 204. The shaped lateral edges 205 may reduce shear stress between an epidermis of a patient and the dressing bolster 204. Other dimensions, steps, and processes may be used.

In some illustrative embodiments, the dressing bolster 204 may be manufactured from a foam block of Granufoam® material. The Granufoam® material may be, for example, a foam block having the dimensions of 1.21 meters×1.8 meters×0.5 meters. The foam block may be cut to have a 19 millimeter height, and a saw may be used to form lateral grooves, such as the flexibility notches 218, in the foam block. A dry layer, such as the comfort layer 210, may be laminated or otherwise attached to the second, inward facing side 208 of the dressing bolster 204. The foam block may be cut, for example, utilizing a die cutter to form a plurality of individual dressing bolsters 204.

A sealing subsystem 222 may provide a fluid seal over the dressing assembly 202 and at least a portion of an epidermis of a patient. The sealing subsystem 222 may include a sealing member 224. The sealing member 224 may be formed with an upper drape portion or first sealing member portion 226 and a lower drape portion or second sealing member portion 228. The first sealing member portion 226 may extend over the first side 206 of the dressing bolster 204 to form a drape flange, or drape extension 230. The drape extension 230 has a first side 232 and a second, inward-facing side 233. The second, inward-facing side 233 of the drape extension 230 may be adapted to face a tissue site of a patient as described above. An aperture 234 may be formed on the first sealing member portion 226. The aperture 234 may provide fluid communication with a conduit interface (not shown). The conduit interface may be analogous to the conduit interface 138 in FIG. 1.

The second sealing member portion 228 may have a first side 236 and a second, inward-facing side 237 adapted to face a tissue site as described above. The second, inward-facing side 233 of the drape extension 230 may be placed on the first side 236 of the second sealing member portion 228, and may be coupled to the first side 236 by an attachment device 238. The attachment device 238 may be, for example, an adhesive, a bond, a weld (e.g., ultrasonic or RF weld), cements, stitching, staples, or other coupling device. The second sealing member portion 228 may include an attachment apparatus on the second, inward-facing side 237 as described below. The second sealing member portion 228 may also include a treatment area aperture 240, depicted in FIG. 5, that may be adapted to permit fluid communication through the second sealing member portion 228 and, for example, between a tissue site and the dressing bolster 204. The treatment area aperture 240 may also provide an opening for at least a portion of the dressing bolster 204, or the comfort layer 210, to be positioned directly against an epidermis and/or a tissue site of a patient.

The first sealing member portion 226 may include a plurality of folds 220 or bellows to facilitate movement as described above. The folds 220 may allow the first sealing member portion 226 to expand. For example, if the dressing assembly 202 is used on a joint, when the joint is flexed, additional drape material from the folds 220 may be released to facilitate movement of the first sealing member portion 226. The folds 220 may also be formed as ridges having the cross-sectional shape of an accordion that provides additional drape material when flattened or stretched, for example.

One or more release members 242 may be releasably coupled to the first side 236 of the second sealing member portion 228, such as, for example, with an adhesive (not shown) applied on at least a portion of the first side 236. Four of the release members 242 are shown in the illustrative embodiment of FIG. 3. The release members 242 may provide stiffness to the second sealing member portion 228, and may cover the adhesive or other attachment apparatus to provide a grasping surface during deployment of the dressing assembly 202. The release members 242 may be casting paper or a film held on the first side 236 of the second sealing member portion 228.

The first side 236 of the second sealing member portion 228 may include an adhesive 244 adapted to retain the dressing bolster 204 against the second sealing member portion 228 during assembly and usage. A center release member 246 may cover and protect the adhesive 244 prior to assembly. The release members 242 that may provide stiffness to the sealing member 224 during deployment may be positioned outboard of the adhesive 244 on the first surface 236 of the second sealing member portion 228.

The dressing assembly 202 may include a sealing ring 248. Analogous to the sealing ring 117, the sealing ring 248 may help seal any wrinkles or discontinuities in the epidermis or drape that might otherwise cause leaks. The sealing ring 248 may be, for example, positioned to cover a portion of the second, inward-facing side 237 of the second sealing member portion 228. The sealing ring 248 may be coupled directly to the dressing assembly 202, or coupled with an optional sealing-ring attachment device 249, such as an acrylic adhesive, cement, or other coupling device. In other embodiments, the sealing ring 248 may be coupled to the second inward-facing side 208 of the dressing bolster 204, and/or to an adjacent layer, such as the comfort layer 210.

The sealing ring 248 may straddle an edge of the dressing bolster 204, or otherwise extend beyond an edge of the dressing bolster 204, as depicted in FIG. 4. In other embodiments, the dressing bolster 204 may entirely overlap the sealing ring 248 as suggested in FIG. 8. While reference is made to a "ring," discrete members, including linear members, may make up the sealing ring 248.

The sealing ring 248 may comprise a sealing material, such as, for example, any of the sealing materials previously described in connection with the sealing ring 117, or other material that provides initial tack between the dressing assembly 202 and an epidermis of a patient. Further, the sealing ring 248 may have a durometer, such as a material softness or hardness, between about 20 Shore 00 to about 90 Shore OO. In some embodiments, the durometer of the sealing ring 248 may be between about 70 Shore 00 to about 80 Shore OO. The sealing ring 248 may have a modulus of elasticity that falls between the modulus of elasticity of the second sealing member portion 228 and the modulus of elasticity of a tissue site and/or epidermis of a patient. As shown in FIG. 4, the sealing ring 248 may have a thickness 250 and a width 252. The thickness 250 of the sealing ring 248 may be between about 0.3 millimeters to about 2.5 millimeters. In some embodiments, the thickness 250 may be between about 0.7 millimeters to about 1.25 millimeters. The width 252 of the sealing ring 248 may be between about 10 millimeters to about 30 millimeters. Other dimensions are possible. In some illustrative embodiments, the thickness 250 may be about 0.7 millimeters and the width 252 may be about 20 millimeters. Further, in some embodiments, the width 252 of the sealing ring 248 may extend beyond an edge of the dressing bolster 204 by about 10 millimeters and overlap the dressing bolster 204 by about 10 millimeters.

In some embodiments, the second sealing member portion 228 may have a thickness 229 between about 0.178 millimeters to about 0.254 millimeters, or about 7 mils to about 10 mils. The ratio of the sealing ring thickness 250 to the sealing member thickness 229 may be between about 2.75 to about 7.03.

The sealing ring 248 may include fenestrations or apertures. In some embodiments, the sealing ring 248 may comprise a patterned sealing material on the second, inward-facing side 214 of the comfort layer 210, or on the second, inward-facing side 208 of the dressing bolster 204. The pattern may be, for example, spaced islands, crossing lines of sealing material, or any other suitable pattern.

The sealing ring 248 may function as a two-sided gasket that may provide a seal between the dressing assembly 202 and a tissue site and/or epidermis of a patient. For example, the sealing ring 248 may provide a seal between the dressing bolster 204, the comfort layer 210, or the second sealing member portion 228 and a tissue site and/or epidermis of a patient. The sealing ring 248 may absorb perspiration or other fluids from a tissue site. Further, the sealing ring 248 may help distribute shear forces created, for example, by the application of reduced pressure at the interface of the dressing bolster 204 and a tissue site and/or epidermis of a patient.

As shown in FIG. 4, a portion of the second, inward-facing side 237 of the second sealing member portion 228 may be covered with a sealing apparatus or device 254, such as an adhesive. With reference to FIGS. 4 and 5, when in the pre-deployment state, the sealing device 254 may be covered by a bottom release member 256 and side release members 258.

The bottom release member 256 may cover and protect, for example, the sealing device 254 and the sealing ring 248. The side release members 258 may also cover and protect the sealing device 254. Similar to the release members 242, the side release members 258 may provide a grasping surface for a user to facilitate deployment of the dressing assembly 202. The release members 242, the bottom release member 256, and/or the side release members 258 may be comprised of a polar semi-crystalline polymer, such as, for example, polyethylene terephthalate (PET). Use of a polar semi-crystalline polymer for the release members 242, the bottom release member 256, and/or the side release members 258 may substantially preclude wrinkling or other deformation of the dressing assembly 202. Any deformation of the release members 242, the bottom release member 256, and/or the side release members 258 may cause wrinkling or deformation of a component of the dressing assembly 202. The polar semi-crystalline polymer is highly orientated and resistant to softening, swelling, or other deformation that may occur when brought into contact with components of the dressing assembly 202, or when subjected to temperature or environmental variations, or sterilization. Thus, for example, when the polar semi-crystalline polymer is used in combination with the hydrocolloid described above for the sealing ring 248, the polar semi-crystalline polymer may not deform when in contact with the compounding ingredients of the hydrocolloid. In some embodiments, the release members 242, the bottom release member 256, and/or the side release members 258 may be configured to resist deformation when exposed to temperature variations between about 40 degrees Celsius to about 60 degrees Celsius, and gamma sterilization doses between about 25 kGy to about 45 kGy.

Continuing with FIGS. 3-5, according to an illustrative embodiment of operation, the bottom release member 256 may be removed to expose the sealing device 254 on the second, inward-facing side 237 of the second sealing member portion 228. Removal of the bottom release member 256 may also expose a second, inward-facing surface 247 of the sealing ring 248. The sealing device 254 and/or the second, inward-facing surface 247 of the sealing ring 248 may be placed against a portion of an epidermis of a patient and around a tissue site that may include a linear wound as described above. The side release members 258 may be removed after applying the second sealing member portion 228. Similarly, the release members 242 on the first side 236 of the second sealing member portion 228 may be removed after applying the second sealing member portion 228. A conduit interface may be coupled to the aperture 234 in the first sealing member portion 226, and reduced pressure may be delivered to the dressing assembly 202.

Regarding the manufacture of the systems and components described above, in applying and coupling a sealing member to a dressing bolster, a press may be utilized to remove any wrinkles in the sealing member. Further, the medical bolster material of the shaped dressing assembly may be cut using a die cutter, or by hand with a router.

Figure 6B:
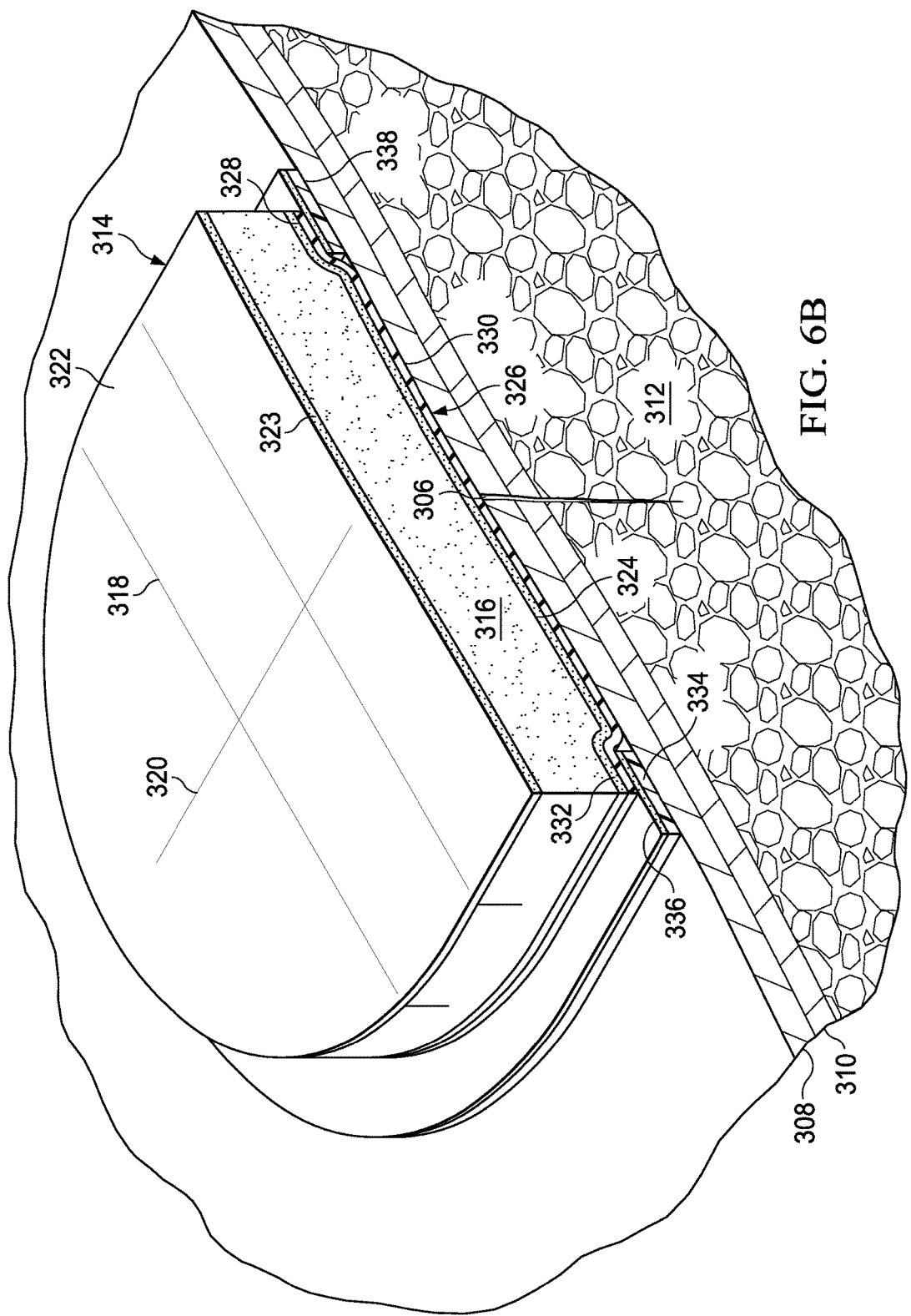
Figure 6C:
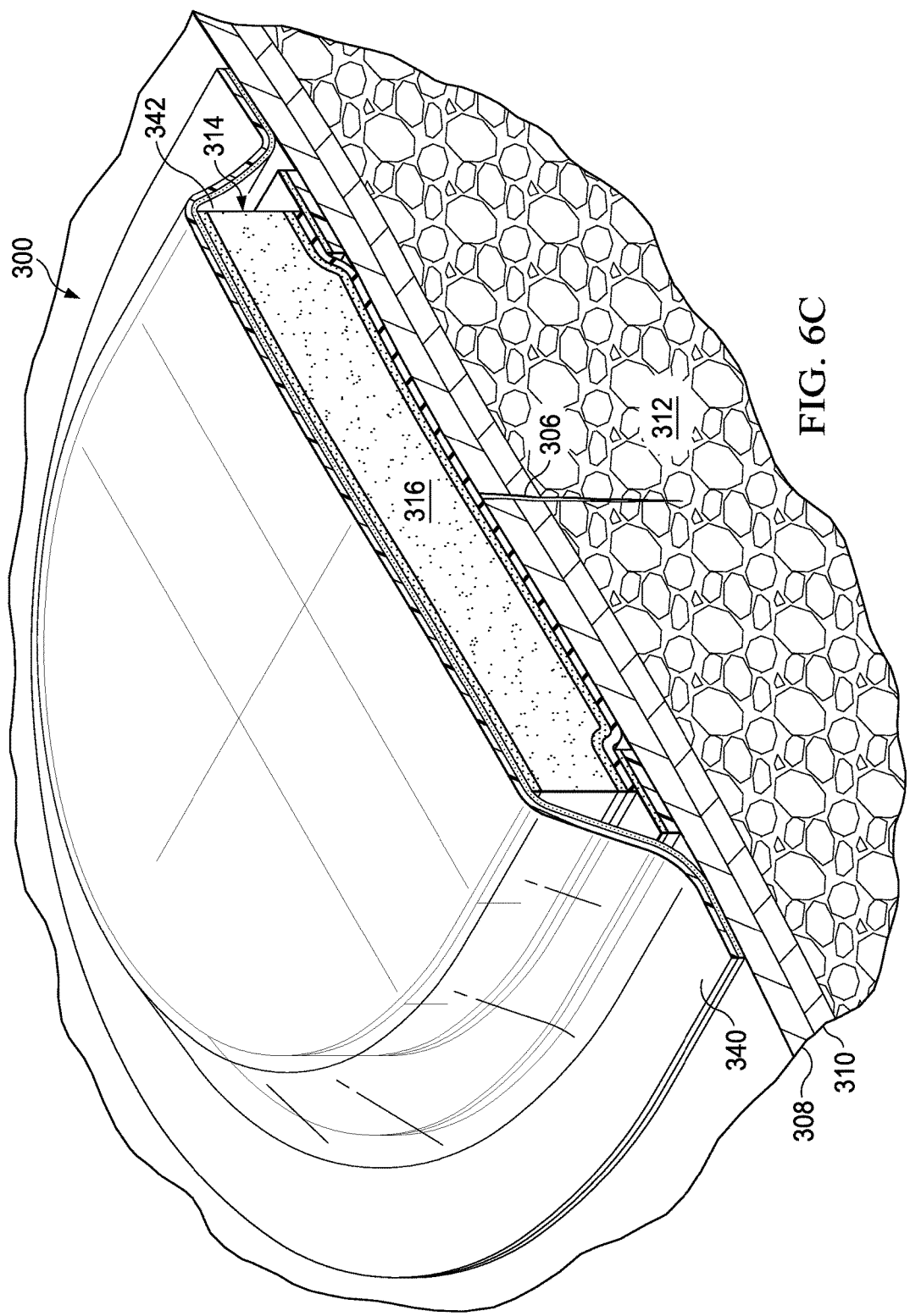

Referring now primarily to FIGS. 6A-6C, presented is another illustrative embodiment of a portion of a treatment system 300. FIGS. 6A-6C depict the treatment system 300 assembled in stages at a tissue site, such as a linear wound 306. In FIG. 6A, a closure device 302, such as, for example, stitches 304, close the linear wound 306. Other closure devices 302, such as epoxy or staples may be utilized to close the linear wound 306. The linear wound 306 may include a portion through an epidermis 308, dermis 310, and subcutaneous tissue 312 of a patient.

Referring now to FIG. 6B, after the linear wound 306 is closed or prepared as described above, a dressing assembly 314 may be disposed proximate to the linear wound 306. The dressing assembly 314 may include a dressing bolster 316. The dressing bolster 316 may be formed from the bolster or manifold materials previously mentioned. The dressing bolster 316 may include a plurality of lateral notches 318 and one or more longitudinal notches 320. The dressing bolster 316 has a first side 322 and a second, inward-facing side 324. The first side 322 may include an adhesive layer 323. The adhesive layer 323 may help secure a sealing member 340 thereto, as shown in FIG. 6C.

The dressing assembly 314 may include a comfort layer 326. The second, inward-facing side 324 of the dressing bolster 316 may be covered with the comfort layer 326. The comfort layer 326 has first side 328 and a second, inward-facing side 330. The first side 328 of the comfort layer 326 may be coupled by an attachment device 332, such as, for example, a heat bond, adhesive, weld, or other attachment device, to the second, inward-facing side 324 of the dressing bolster 316.

The dressing assembly 314 may include a sealing ring 334. The sealing ring 334 may be coupled, at least in part, to the second, inward-facing side 330 of the comfort layer 326. The sealing ring 334 may be analogous to the sealing ring 117 of FIG. 2 and the sealing ring 248 of FIGS. 3-5. For example, the sealing ring 334 may comprise any of the sealing materials previously described in connection with the sealing ring 117 and the sealing ring 248. The sealing ring 334 may adhere directly to the comfort layer 326, or may be coupled with a sealing-ring attachment device 336 to the comfort layer 326. The sealing-ring attachment device 336 may be, for example, acrylic adhesive, cement, or other suitable attachment device. The sealing ring 334 and/or the sealing ring attachment device 336 may be co-extensive with the comfort layer 326, or may extend beyond a lateral edge of the comfort layer 326 and the dressing bolster 316.

Prior to application, a second, inward-facing surface 338 of the sealing ring 334 may be covered by a release member or release liner (not shown). When the release liner is removed, the sealing ring 334 may be centered about the linear wound 306 for deployment. A release member or release liner (not shown) may also temporarily cover a portion of the sealing ring 334 and/or sealing ring attachment device 336 to provide a grasping surface during deployment of the dressing assembly 314. The release liner or release member covering, for example, the sealing ring 334, the sealing ring attachment device 336, and/or other components of the dressing assembly 314 may be analogous to the release members 242, 256, and 258 of FIGS. 3-5. For example, the release members may be positioned on the dressing assembly 314 analogous to the release members 242, 256, and 258. Further, the release members on the dressing assembly 314 may be comprised of any of the materials previously described for the release members 242, 256, and 258, such as, for example, a polar semi-crystalline polymer or polyethylene terephthalate (PET). As described above, use of a polar semi-crystalline polymer such as PET as a release member on the dressing assembly 314 may substantially preclude deformation of the dressing assembly 314. In another embodiment, the sealing ring 334 may be separately applied around the linear wound 306 before the dressing bolster 316 is applied thereto.

Referring now to FIG. 6C, a sealing member 340 may be disposed over the dressing assembly 314 and a portion of the epidermis 308 to form a sealed space 342 between the dressing assembly 314 and the linear wound 306. Analogous to the aperture 234 in FIG. 3, an aperture (not shown) may be formed or preformed in the sealing member 340. A conduit interface (not shown), analogous to conduit interface 138 described above, may be coupled to the sealing member 340 to provide fluid communication with the sealed space 342 through the aperture. Further, a reduced-pressure source (not shown), analogous to the reduced-pressure source 144 in FIG. 1, may be coupled to the conduit interface to provide reduced pressure to the sealed space 342 to treat the linear wound 306. A delivery conduit (not shown), analogous to the delivery conduit 148 in FIG. 1, may be utilized for coupling the reduced pressure source to the conduit interface. Reduced pressure may be applied to the tissue site, such as the linear wound 306, and fluid may be extracted from the tissue site and into the dressing assembly 314. The fluid from the tissue site may be absorbed into the sealing ring 334. The fluid from the tissue site may be wicked or otherwise communicated in a lateral direction within the dressing assembly 314 toward the sealing ring 334.

Figure 7:
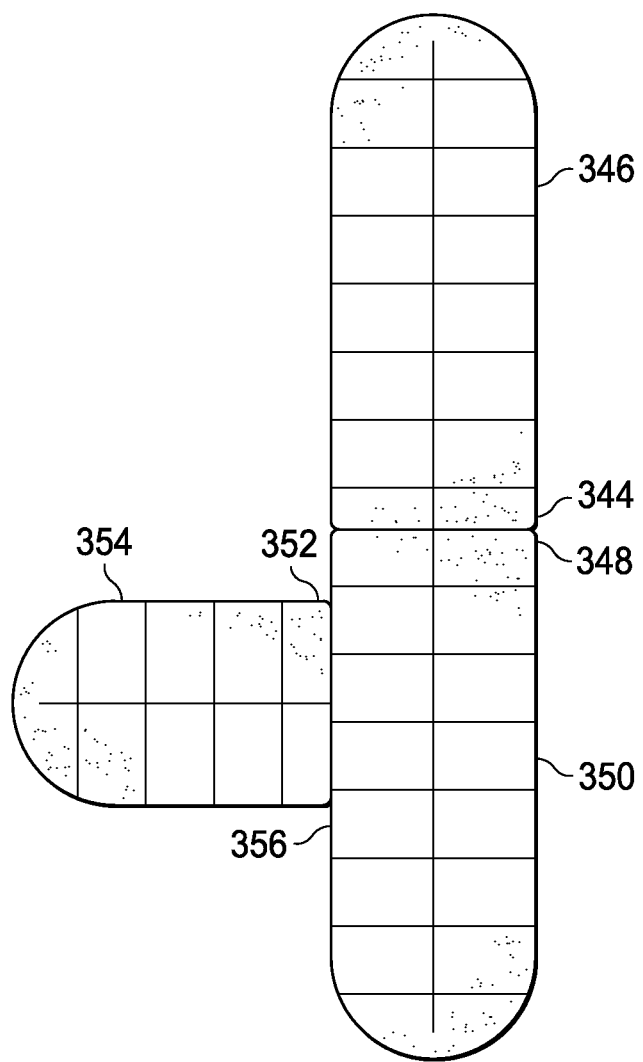
FIG. 7 is a top view of a portion of an illustrative embodiment of a treatment system for treating a tissue site.

The dressing assembly 314 may be cut to accommodate different sizes of linear wounds 306 prior to being disposed on the linear wound 306 and covered with the sealing member 340. As shown in FIG. 7, for lengthy linear wounds 306, or multiple linear wounds 306 in a vicinity, more than one dressing assembly 314 may be used. Continuing with FIG. 7, a first longitudinal end 344 of a first dressing assembly 346 may be cut to have a flat surface. A first longitudinal end 348 of a second dressing assembly 350 may be cut or otherwise formed with a flat surface. The first longitudinal end 344 of the first dressing assembly 346 may be placed proximate to and abutting the first longitudinal end 348 of the second dressing assembly 350. The sealing rings (not shown but analogous to sealing ring 334) below the first dressing assembly 346 and the second dressing assembly 350 may coalesce or combine to form an integral sealing ring.

A first longitudinal end 352 of a third dressing assembly 354 may be placed proximate to and abutting a lateral end or edge 356 of the second dressing assembly 350. Once the combination of dressing assemblies is arranged, the dressing assemblies 346, 350, 354 may be covered with a sealing member (not shown but analogous to sealing member 340 in FIG. 6C) to form a sealed space that contains the dressing assemblies 346, 350, 354. Reduced pressure may be then be applied to the sealed space to treat the linear wound or wounds.

Figure 8:
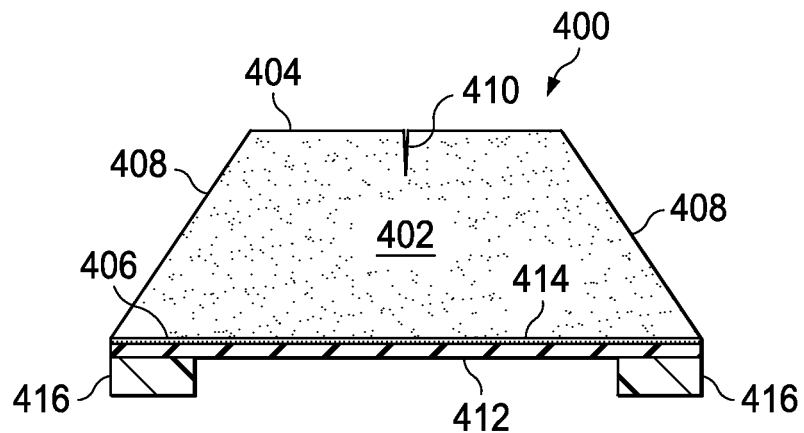
FIG. 8 is a cross-section of an illustrative embodiment of a dressing assembly.

Referring now primarily to FIG. 8, depicted is a cross-section of an illustrative embodiment of a dressing assembly 400. The dressing assembly 400 may be used with treatment systems as described above, such as the treatment system 200. The dressing assembly 400 may include a dressing bolster 402. The dressing bolster 402 has a first side 404, a second, inward-facing side 406, and lateral edges 408. As with the previously presented dressing assemblies, the lateral edges 408 may take any shape, but are shown formed with approximately a 45 degree angle with respect to the second, inward-facing side 406. In the cross-section, a longitudinal notch 410 is visible. In addition, lateral notches (not shown) may be included on the first side 404, and notches (not shown) may be added to the lateral edges 408. The longitudinal notch 410 and any other notches help provide flexibility to the dressing assembly 400.

A comfort layer 412 may be coupled by an attachment device 414 to the second, inward-facing side 406 of the dressing bolster 402. A sealing ring 416 may be coupled to the comfort layer 412. The sealing ring 416 may be formed from the sealing materials previously mentioned. The sealing ring 416 may be coupled directly to the comfort layer 412, or may be attached to the comfort layer 412 by an attachment device, such as an acrylic adhesive (not shown).

Analogous to the previously described embodiments, in operation, the dressing assembly 400 may be placed over and about a linear wound and then covered with a sealing member to form a sealed space. Reduced pressure may then be delivered to the sealed space to treat the linear wound.

Figure 9:
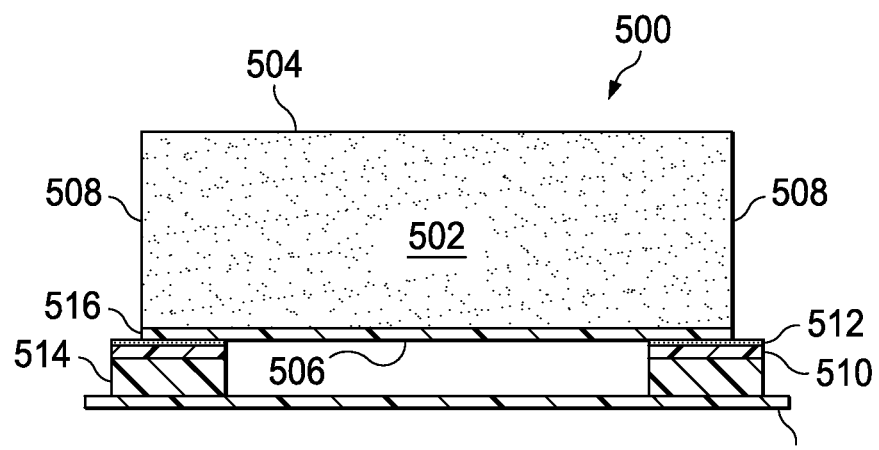
FIG. 9 is a cross-section of an illustrative embodiment of a dressing assembly.

Referring now primarily to FIG. 9, depicted is a cross-section of another embodiment of a dressing assembly 500. The dressing assembly 500 may be analogous to the dressing assembly 400 of FIG. 8. The dressing assembly 500 includes a dressing bolster 502 having a first side 504 and a second, inward-facing side 506. The lateral edges 508 are substantially orthogonal to the second, inward-facing side 506. However, analogous to the dressing bolster 402 of FIG. 8, the lateral edges 508 of the dressing bolster 502 may have any angle or shape. In this embodiment, a sealing ring 514 may be laminated or coupled to a drape ring 510. The drape ring 510 may assist with positioning and manipulating the sealing ring 514 during assembly. The drape ring 510 may be coupled by an attachment device 512 to the second, inward-facing side 506 of the dressing bolster 502, or to an inward-facing side of a comfort layer 516. The sealing ring 514 may be covered by a release liner 518 prior to use.

In another embodiment (not explicitly shown), an attachment device, such as an adhesive, may be applied to the second, inward-facing side of a sealing ring to provide tackiness or enhanced tackiness between the sealing ring and an epidermis of a patient. The attachment device may be particularly beneficial when the sealing ring comprises a harder hydrocolloid than those previously mentioned, or when applied in cold conditions to provide time for the sealing material to warm up and become adequately tacky.

Although the subject matter of this disclosure has been provided by way of example in the context of certain illustrative, non-limiting embodiments, various changes, substitutions, permutations, and alterations can be made without departing from the scope of this disclosure as defined by the appended claims. Any feature described in connection to any one embodiment may also be applicable to any other embodiment. As such, the benefits and advantages described above may relate to one embodiment or may relate to several embodiments. Further, the steps of the methods described herein may be carried out in any suitable order, or simultaneously where appropriate.

We claim:

1. A dressing assembly, comprising:
a dressing bolster comprising foam and having a first side and a second side;
a comfort layer having a first side and a second side, the first side of the comfort layer coupled to the second side of the dressing bolster;
a sealing ring comprising an absorbent and having a first side and a second side, the first side of the sealing ring coupled to the second side of the comfort layer and positioned around a circumference of the dressing bolster, at least a portion of the second side of the comfort layer being exposed; and
a removable bottom release member having a release agent configured to contact the sealing ring and comprising a polar semi-crystalline polymer configured to resist deformation when positioned in contact with the second side of the sealing ring.

2. The dressing assembly of claim 1, wherein the sealing ring comprises a hydrocolloid including the absorbent.

3. The dressing assembly of claim 1, wherein the absorbent comprises carboxy methyl cellulose.

4. The dressing assembly of claim 1, wherein the dressing bolster has a lateral edge substantially aligned with a lateral edge of the comfort layer.

5. The dressing assembly of claim 1, wherein the sealing ring is positioned at a lateral edge of the dressing bolster.

6. The dressing assembly of claim 1, wherein the portion of the second side of the comfort layer that is exposed is configured to be positioned directly against the tissue site, the sealing ring being configured to surround the tissue site and the portion of the comfort layer that is exposed.

7. The dressing assembly of claim 1, wherein the sealing ring is comprised of a sealing material having a hardness between about 70 to about 80 Shore, type OO.

8. The dressing assembly of claim 1, wherein the sealing ring has a thickness $T_{sr}$ between about 0.7 millimeters to about 1.25 millimeters.

9. The dressing assembly of claim 1, wherein the sealing ring extends beyond a lateral edge of the dressing bolster and a lateral edge of the comfort layer, the dressing assembly further comprising a release member in contact with at least a portion of the first side of the sealing ring beyond the lateral edge of the dressing bolster and the lateral edge of the comfort layer.

10. The dressing assembly of claim 1, wherein the dressing bolster is comprised of a reticulated open-cell foam.

11. The dressing assembly of claim 1, wherein the comfort layer is selected from the group consisting of a woven material, a non-woven material, a polyester knit material, and a fenestrated film.

12. The dressing assembly of claim 1, wherein the dressing bolster has longitudinal cuts and lateral cuts disposed in the first side of the dressing bolster, the longitudinal cuts positioned normal to the lateral cuts.

13. The dressing assembly of claim 1, wherein the bottom release member is configured to cover the sealing ring and to be removable from the sealing ring.

14. The dressing assembly of claim 13, wherein the bottom release member is comprised of polyethylene terephthalate.

15. A method for treating a tissue site, comprising:
providing a dressing assembly, comprising:
a dressing bolster,
a comfort layer coupled to the dressing bolster,
a sealing ring coupled to the comfort layer, and
a bottom release member having a release agent configured to contact the sealing ring and comprising a polar semi-crystalline polymer positioned in contact with the sealing ring and configured to resist deformation;
removing the bottom release member;
disposing the dressing assembly proximate to the tissue site;
covering the dressing assembly with a sealing member to form a sealed space between the dressing assembly and the tissue site;
extracting fluid from the tissue site into the dressing assembly; and
absorbing the fluid from the tissue site into the sealing ring.

16. The method of claim 15, wherein extracting the fluid comprises applying reduced pressure to the sealed space.

17. The method of claim 15, further comprising communicating the fluid in a lateral direction within the dressing assembly toward the sealing ring.

18. The method of claim 15, further comprising wicking the fluid in a lateral direction within the dressing assembly toward the sealing ring.

19. The method of claim 15, wherein the sealing ring comprises an absorbent.

20. The method of claim 15, wherein the sealing ring comprises a hydrocolloid including an absorbent.

21. The method of claim 19, wherein the absorbent comprises carboxy methyl cellulose.

22. The method of claim 15, wherein the sealing ring is positioned at a lateral edge of the dressing bolster and configured to surround the tissue site.

23. The method of claim 15, wherein the sealing ring is positioned around at least a portion of the comfort layer that is exposed and configured to be positioned directly against the tissue site.

* * * * *